United States Patent
Wasserman et al.

(10) Patent No.: US 9,914,797 B2
(45) Date of Patent: Mar. 13, 2018

(54) ALKALI-SWELLABLE CROSSLINKED ACRYLATE COPOLYMER, METHODS OF MANUFACTURE THEREOF, AND COMPOSITION COMPRISING THE SAME

(71) Applicants: UNION CARBIDE CHEMICALS & PLASTICS TECHNOLOGY LLC, Midland, MI (US); ROHM AND HAAS CHEMICALS LLC, Philadelphia, PA (US)

(72) Inventors: Eric P. Wasserman, Hopewell, NJ (US); Marianne P. Creamer, Warrington, PA (US)

(73) Assignees: ROHM AND HAAS CHEMICALS LLC, Philadelphia, PA (US); UNION CARBIDE CHEMICALS & PLASTICS TECHNOLOGY LLC, Midland, MI (US)

( * ) Notice: Subject to any disclaimer, the term of this patent is extended or adjusted under 35 U.S.C. 154(b) by 64 days.

(21) Appl. No.: 15/035,513

(22) PCT Filed: Sep. 19, 2014

(86) PCT No.: PCT/US2014/056429
§ 371 (c)(1),
(2) Date: May 10, 2016

(87) PCT Pub. No.: WO2015/073117
PCT Pub. Date: May 21, 2015

(65) Prior Publication Data
US 2016/0272748 A1    Sep. 22, 2016

Related U.S. Application Data

(60) Provisional application No. 61/903,578, filed on Nov. 13, 2013.

(51) Int. Cl.
| | | |
|---|---|---|
| C08F 251/02 | (2006.01) |
| A61Q 19/10 | (2006.01) |
| C08F 299/00 | (2006.01) |
| A61K 8/81 | (2006.01) |
| A61K 8/91 | (2006.01) |

(52) U.S. Cl.
CPC .......... *C08F 251/02* (2013.01); *A61K 8/8152* (2013.01); *A61K 8/91* (2013.01); *A61Q 19/10* (2013.01); *C08F 299/00* (2013.01); *A61K 2800/48* (2013.01)

(58) Field of Classification Search
CPC ........ C08F 251/02; C08F 299/00; A61K 8/91; A61K 8/8152; A61K 2800/48; A61Q 19/10
See application file for complete search history.

(56) References Cited

U.S. PATENT DOCUMENTS

| | | | |
|---|---|---|---|
| 5,840,789 A | 11/1998 | Verstrat et al. | |
| 5,886,124 A * | 3/1999 | Kightlinger | C08F 251/02 527/312 |
| 7,217,752 B2 | 5/2007 | Schmucker-Castner et al. | |
| 2002/0042448 A1 | 4/2002 | Sorrentino et al. | |
| 2013/0189198 A1 | 7/2013 | Tamareselvy | |

FOREIGN PATENT DOCUMENTS

| | | |
|---|---|---|
| CA | 745657 A | 11/1966 |
| CA | 2192381 A1 | 6/1997 |
| EP | 2514777 A1 | 10/2012 |
| EP | 2532682 A1 | 12/2012 |
| JP | 50003799 B1 | 2/1975 |
| WO | WO 2012/047957 A1 * | 4/2012 |

OTHER PUBLICATIONS

US 7,851,571, 12/2010, Rodrigues et al. (withdrawn)
Natrosol Hydroxyethylcellulose A Nonionic Water-Soluble Polymer; Hercules Incorporated, 1999, 24 pages.
International Search Report for International Application Serial No. PCT/US2014/056429; International Filing Date Sep. 19, 2014; Report dated Dec. 5, 2014 (4 pages).
S.N. Bhattacharyya et al., "Graft Copolymerization Onto Cellulosics," Prog. Polym. Sci., vol. 10, pp. 171-270, 1984.
Written Opinion for International Application Serial No. PCT/US2014/056429; International Filing Date Sep. 19, 2014; Report dated Dec. 5, 2014 (4 pages).

* cited by examiner

*Primary Examiner* — Robert Jones, Jr.
(74) *Attorney, Agent, or Firm* — Cantor Colburn LLP (57) ABSTRACT

A rheology modifier including: a water-dispersible, alkali-swellable crosslinked polyacrylate copolymer including 0.02 to 5 weight percent of polysaccharide grafts, based on a total weight of the copolymer.

19 Claims, 4 Drawing Sheets

ALKALI-SWELLABLE CROSSLINKED ACRYLATE COPOLYMER, METHODS OF MANUFACTURE THEREOF, AND COMPOSITION COMPRISING THE SAME

CROSS-REFERENCE TO RELATED APPLICATIONS

This application is a U.S. national stage application of International Application No. PCT/US2014/056429 entitled "ALKALI-SWELLABLE CROSSLINKED ACRYLATE COPOLYMER, METHODS OF MANUFACTURE THEREOF, AND COMPOSITION COMPRISING THE SAME," which has an international filing date of Sep. 19, 2014, and which claims priority to U.S. Provisional Patent Application No. 61/903,578, filed on Nov. 13, 2013, the contents of which are incorporated herein by reference in their entirety.

BACKGROUND

This invention relates to an alkali-swellable crosslinked acrylate copolymer, methods of manufacture thereof, and a composition comprising the alkali-swellable crosslinked acrylate copolymer. The copolymer is useful to thicken compositions to provide desirable storage and flow properties.

Rheology modifiers are used to control the viscosity of a variety of consumer and commercial products, including laundry detergents and personal cleaning formulations, such as shampoo and body wash. The rheology modifier may be used to thicken a formulation to provide a more appealing viscosity and to provide desirable flow characteristics, for example to provide a consistency suitable for squeezing through an orifice. Rheology modifiers can also be used to suspend gas bubbles, encapsulated additives, or solid particles within a formulation for extended periods of time, effectively preventing settling.

Rheology modifiers can be natural or synthetic. Modified natural compounds which have been utilized in the art for many years include starch, cellulose, alginate, and protein. Synthesized polymeric thickeners include acrylic-based polymers derived from acrylic acid or acrylate esters among others. The rheology modifier may be an alkali-swellable polymer. Alkali-swellable polymers thicken upon neutralization with a base, and thus provide desirable formulation properties because they are easily processed.

The viscosity of a formulation may be enhanced by addition of a salt, such as sodium chloride, sodium sulfate, or ammonium chloride, or a polymer such as cellulose, to the formulation. Many thickeners, including salts and some polymers, provide Newtonian properties, that is, a relatively invariant viscosity across a wide range of shear rate. However Newtonian properties are not suitable for many applications because if an amount of the salt or the polymer is used to provide a viscosity at low shear rates sufficient to suspend gas bubbles, encapsulated additives, or solid particles, the formulation also has too high of a viscosity at higher shear rates, rendering it too thick to pour.

Polymers having long alkyl chains, e.g., associative thickeners, can also be used to suspend gas bubbles, encapsulated additives, or solid particles. Associative thickeners are understood to form crosslinks or other intermolecular associations between hydrophobic alkyl groups on different chains of the polymer. However associative thickeners are expensive due to the use of exotic surfactant-like monomers or chain terminators and thus can be economically undesirable. Further, in higher concentrations associative thickeners can result in coagulation when used in emulsion polymerization.

Thus there remains a need for improved materials and methods to control rheology.

SUMMARY

Disclosed is a rheology modifier including a water-dispersible, alkali-swellable crosslinked polyacrylate copolymer including 0.02 to 5 weight percent of polysaccharide grafts, based on a total weight of the copolymer.

Also disclosed is method of preparing a rheology modifier, the method including: providing an emulsion comprising a water-dispersible, alkali-swellable crosslinked polyacrylate copolymer; and contacting the emulsion with an aqueous grafting solution including a water-dispersible polysaccharide in the presence of a free-radical initiator to form an alkali-swellable crosslinked polysaccharide-grafted polyacrylate copolymer including 0.1 to 5 weight percent of polysaccharide grafts, based on a total weight of the copolymer, to form the rheology modifier.

Also disclosed is a composition including the rheology modifier.

BRIEF DESCRIPTION OF THE DRAWINGS

The above and other aspects, advantages and features of this disclosure will become more apparent by describing in further detail exemplary embodiments thereof with reference to the accompanying drawings, in which.

DETAILED DESCRIPTION

Disclosed is a rheology modifier comprising a water-dispersible, alkali-swellable crosslinked polyacrylate copolymer comprising 0.02 to 5 weight percent (wt %) of polysaccharide grafts, based on a total weight of the copolymer. The polysaccharide-grafted polyacrylate copolymer provides improved low-shear viscosity and improved storage modulus. By providing improved shear-thinning, the disclosed rheology modifiers provide improved suspension of included gases, encapsulated additives, or solid particles if present in a formulation, while also providing a suitable pour-shear viscosity, thereby providing desirable dispensing properties. The neutralized copolymer is water-dispersible, by which is meant that it forms a visually clear, stable, and homogeneous dispersion when the acidic groups in its composition are neutralized with base.

The polysaccharide may comprise a cellulose ether, a gum, a starch, or a combination thereof. Representative cellulose ethers include hydroxyethyl cellulose, hydroxypropyl cellulose, hydroxyethyl methyl cellulose, hydroxypropyl methyl cellulose, hydroxypropylhydroxyethyl cellulose, carboxymethyl cellulose, carboxyethyl cellulose, or a combination thereof. Hydroxyethyl cellulose is specifically mentioned. Representative gums include guar gum, locust bean gum, xanthan gum, hydroxyethyl guar gum, methyl guar gum, ethyl guar gum, hydroxypropyl guar gum, hydroxyethylmethyl guar gum, hydroxypropylmethyl guar gum, or a combination thereof. Representative starches include methyl starch, ethyl starch, hydroxyethylmethyl starch, hydroxypropyl starch, hydroxypropylmethyl starch, or a combination thereof.

The polysaccharide may have a molecular weight, e.g., a weight average molecular weight, of 50,000 to 1,500,000 Daltons (Da), specifically 100,000 to 1,000,000 Da, more specifically 200,000 to 800,000 Da. The molecular weight of the polysaccharide may be derived from an intrinsic viscosity of the polysaccharide. The Brookfield viscosity of a 2% aqueous solution of the polysaccharide may be 1.5 to 5000 centipoise, specifically 3 to 2000 centipoise, more specifically 5 to 1000 centipoise, when determined at 25° C. and 30 revolutions per minute (rpm). The polysaccharide may have a degree of polymerization of 300 to 5000, specifically 400 to 4500, more specifically 500 to 4000.

The polysaccharide grafts may be present in an amount of 0.02 to 5 wt %, specifically 0.05 to 4, more specifically 0.1 to 3 wt %, based on a total weight of the polysaccharide-grafted copolymer. The foregoing content of polysaccharide grafts may be provided by polymerization of an emulsion comprising 0.1 to 5 wt % of the polysaccharide, based on a total weight of monomers. While not wanting to be bound by theory, it is understood that graft efficiency can be less than 100%, e.g., 20 to 80%, and thus polymerization of an emulsion comprising 0.2 to 5 wt % of the polysaccharide can result in a polysaccharide copolymer comprising 0.1 to 5 wt % of polysaccharide grafts. Use of hydroxyethyl cellulose grafts in an amount of 0.1 to 5 wt %, based on a total weight of the polysaccharide-grafted copolymer, is specifically mentioned.

The water-dispersible, alkali-swellable crosslinked polyacrylate copolymer comprises units derived from an α,β-ethylenically mono-unsaturated carboxylic acid monomer, units derived from an ethylenically unsaturated ester of (meth)acrylic acid, and crosslinks derived from a polyethylenically unsaturated crosslinker. While not wanting to be bound by theory, it is understood that by including at least 20 percent of units derived from the α,β-ethylenically mono-unsaturated carboxylic acid monomer in the copolymer, a water-dispersible, alkali-swellable crosslinked polyacrylate copolymer is provided. The units derived from the α,β-ethylenically mono-unsaturated carboxylic acid monomer may be present in an amount of 20 to 75 wt %, specifically 25 to 70 wt %, more specifically 30 to 65 wt %, based on a total weight of the water-dispersible, alkali-swellable crosslinked polyacrylate copolymer. Also, the units derived from the α,β-ethylenically mono-unsaturated carboxylic acid monomer may be present in an amount of 20 to 75 wt %, specifically 25 to 70 wt %, more specifically 30 to 65 wt %, based on a total weight of the polysaccharide-grafted copolymer. Any suitable α,β-ethylenically mono-unsaturated carboxylic acid monomer may be used. Representative α,β-ethylenically mono-unsaturated carboxylic acid monomers include (meth)acrylic acid, maleic acid, itaconic acid, fumaric acid, crotonic acid, aconitic acid, citraconic acid, or a combination thereof.

The water-dispersible, alkali-swellable crosslinked polyacrylate copolymer also comprises units derived from an ethylenically unsaturated ester of (meth)acrylic acid. Any suitable ethylenically unsaturated ester of (meth)acrylic acid may be used. The ethylenically unsaturated ester of (meth)acrylic acid may be linear or branched and may comprise a C1 to C30 alkyl ester, a C1 to C30 arylalkyl ester, a C1 to C30 hydroxyalkyl ester, a C1 to C30 hydroxyarylalkyl ester, or a combination thereof. Representative ethylenically unsaturated esters of (meth)acrylic acid include methyl (meth)acrylate, ethyl (meth)acrylate, 2-ethylhexyl (meth)acrylate, n-propyl(meth)acrylate, iso-propyl(meth)acrylate, butyl (meth)acrylate, n-amyl(meth)acrylate, iso-amyl(meth)acrylate, benzyl (meth)acrylate, hydroxyethyl(meth)acrylate, hydroxypropyl(meth)acrylate, hydroxybutyl(meth)acrylate, butane diol mono(meth)acrylate, or a combination thereof. Methyl (meth)acrylate is specifically mentioned.

The units derived from the ethylenically unsaturated ester of (meth)acrylic acid may be present in an amount of 20 to 60 wt %, specifically 25 to 55 wt %, more specifically 30 to 50 wt %, based on a total weight of the water-dispersible, alkali-swellable crosslinked polyacrylate copolymer. Also, the units derived from the ethylenically unsaturated ester of (meth)acrylic acid may be present in an amount of 20 to 60 wt %, specifically 25 to 55 wt %, more specifically 30 to 50 wt %, based on a total weight of the polysaccharide-grafted copolymer.

The water-dispersible, alkali-swellable crosslinked polyacrylate copolymer also comprises crosslinks derived from a polyethylenically unsaturated crosslinker having at least two polymerizable ethylenically unsaturated double bonds. Any suitable polyethylenically unsaturated crosslinker may be used. The polyethylenically unsaturated crosslinker can contain 2 to 6 polymerizable ethylenically unsaturated double bonds. The crosslinker may be, for example, a polyfunctional acrylate, such as ethylene glycol di(meth)acrylate, triethylene glycol di(meth)acrylate, 1,3-butylene glycol di(meth)acrylate, 1,4-butylene glycol di(meth)acrylate, 1,6-hexanediol di(meth)acrylate, neopentyl glycol di(meth)acrylate, 1,9-nonanediol di(meth)acrylate, trimethylolpropane tri(meth)acrylate, trimethylolethane tri(meth)acrylate, tetramethylolmethane tri(meth)acrylate, ditrimethylolpropane tetra(meth)acrylate, tetramethylolmethane tetra(meth)acrylate, pentaerythritol tetra(meth)acrylate, dipentaerythritol hexa(meth)acrylate, 1,4-cyclohexanediol dimethacrylate, or a combination thereof. The crosslinker may also be a polyallyl ether, such as pentaerythritol diallyl ether, pentaerythritol triallyl ether, pentaerythritol tetraallyl ether, trimethylolpropane diallyl ether, trimethylolpropane triallyl ether, or a combination thereof. A combination comprising at least one of the foregoing may be used. In an embodiment, the crosslinker may be trimethylolpropane diallyl ether, trimethylolpropane triallyl ether, diallyl phthalate, allyl methacrylate, methylene bis acrylamide, glycol di-(meth) acrylate, triallyl cyanurate, triallyl isocyanurate, or a combination thereof.

The content of crosslinks may be 0.01 to 1 wt %, specifically 0.02 to 0.9 wt %, more specifically 0.04 to 0.8 wt %, based on a total weight of the water-dispersible, alkali-swellable crosslinked polyacrylate copolymer. Also, the content of crosslinks may be 0.01 to 1 wt %, specifically 0.02 to 0.9 wt %, more specifically 0.04 to 0.8 wt %, based on a total weight of the polysaccharide-grafted copolymer.

The water-dispersible, alkali-swellable crosslinked polyacrylate copolymer may further comprise units derived from a vinyl ester. Any suitable vinyl ester may be used. Representative vinyl esters include vinyl acetate, vinyl neodecanoate, vinyl pivalate, vinyl benzoate, vinyl t-butylbenzoate, or a combination thereof. The vinyl ester units, if present, may be included in an amount of 0.1 to 20 wt %, specifically 0.2 to 18 wt %, more specifically 0.4 to 16 wt %, based on a total weight of the water-dispersible, alkali-swellable crosslinked polyacrylate copolymer. Also, the vinyl ester units, if present, may be included in an amount of 0.1 to 20 wt %, specifically 0.2 to 18 wt %, more specifically 0.4 to 16 wt %, based on a total weight of the polysaccharide-grafted copolymer.

The water-dispersible, alkali-swellable crosslinked polyacrylate copolymer may further comprise units derived from a surfactant monomer. Any suitable surfactant monomer may be used. The surfactant monomer may be of Formula (1)

wherein $R_1$ is hydrogen or a C1 to C4 alkyl group, $R_2$ and $R_3$ are each independently a C1 to C4 alkylene group, x and y are each independently 3 to 40, and $R_4$ is a C8 to C20 linear or branched alkyl group. For example, each of $R_2$ and $R_3$ may each independently be a 1,2-ethanediyl group, a 1,2-propanediyl group, or a 1,2-butanediyl group, for example.

The surfactant monomer may be, for example, ceteth-20 methacrylate, laureth-10 methacrylate, steareth-25 methacrylate, beheneth-30 acrylate, polyethylene glycol (DP=30) monododecyl ether methacrylate, or a combination thereof.

The surfactant monomer, if present, may be included in an amount of 0.1 to 20 wt %, specifically 0.2 to 18 wt %, more specifically 0.4 to 16 wt %, based on a total weight of the water-soluble, alkali-swellable crosslinked polyacrylate copolymer. Also, the surfactant monomer, if present, may be included in an amount of 0.1 to 20 wt %, specifically 0.2 to 18 wt %, more specifically 0.4 to 16 wt %, based on a total weight of the polysaccharide-grafted copolymer.

The rheology modifier can be prepared by emulsion polymerization. In emulsion polymerization, a mixture of monomers is emulsified in an aqueous phase, and the emulsified monomers are then polymerized in the presence of a suitable free radical forming initiator to provide a copolymer. The emulsion polymerization can be carried out in a batch process, in a metered monomer addition process, or the polymerization can be started as a batch process and then continued as monomers are continuously metered into the reactor. The addition of the polysaccharide to the reaction mixture may be done continuously from the start of polymerization or in a separate phase following the polymerization of a portion of the monomer mixture in the absence of polysaccharide. If the polysaccharide is added during a second phase of the reaction, an embodiment of the process is to add a portion of the total monomer along with the polysaccharide. In this embodiment, the portion of the monomer added in the second or grafting phase may be 0 to 30 wt %, preferably 1 to 25 wt %, or more preferably 2 to 20 wt % of the total monomer mass. The polysaccharide can be added in the form of a solid powder, a slurry in a non-solvent fluid such as a monomer, or a homogeneous solution. If added as a solution, the solvent may be water and the resulting solution viscosity may be less than 10,000 centipoise. The polysaccharide may be added separately from monomer or pre-mixed with one or more monomers, optionally with water and surfactant. For clarity, additional details of emulsion polymerization which may be determined by one of skill in the art without undue experimentation are omitted herein.

Also disclosed is a method of preparing the rheology modifier, the method comprising: providing an emulsion comprising a water-soluble, alkali-swellable crosslinked polyacrylate copolymer; and contacting the emulsion with an aqueous grafting solution comprising a water-soluble polysaccharide in the presence of a free-radical initiator to form an alkali-swellable crosslinked polysaccharide-grafted polyacrylate copolymer comprising 0.1 to 5 weight percent of polysaccharide grafts, based on a total weight of the polysaccharide-grafted copolymer, to form the rheology modifier.

Any suitable free-radical initiator may be used. Representative free radical initiators include water-soluble inorganic persulfate compounds, such as ammonium persulfate, potassium persulfate, or sodium persulfate; peroxides such as hydrogen peroxide, benzoyl peroxide, acetyl peroxide, or lauryl peroxide; an organic hydroperoxide such as cumene hydroperoxide or t-butyl hydroperoxide; an organic peracid such as peracetic acid; an oil soluble, free radical producing agent such as 2,2'-azobisisobutyronitrile, or a combination thereof. Peroxides and peracids can optionally be activated with reducing agents, such as sodium bisulfite, sodium formaldehyde, or ascorbic acid, a transition metal, hydrazine, or a combination thereof. Representative free-radical polymerization initiators also include water soluble azo polymerization initiators, such as a water soluble 2,2'-azobis(tert-alkyl), such as 2,2'-azobis(2-(4,5-dihydroimidazolyl)propane), 2,2'-azobis(2-methylpropionamidine, or 4,4'-azobis(4-cyanovaleric acid). The free radical initiator may be included in an amount of 0.01 to 5 wt %, based on a total weight of the water-soluble, alkali-swellable crosslinked polyacrylate copolymer and the water soluble polysaccharide.

The rheology modifier may be in the form of an emulsion, and this emulsion may have a solids content of 10 to 60 wt %, specifically 15 to 55 wt %, more specifically 20 to 50 wt %, based on a total weight of the emulsion.

During the contacting to graft the polysaccharide to the water-dispersible, alkali-swellable crosslinked polyacrylate copolymer, the polysaccharide may be added to the copolymer in a time of 5 to 60 minutes, specifically 10 to 50 minutes. A total time from a start of addition of the polysaccharide to completion of the polymerization may be 15 to 120 minutes, specifically 30 to 100 minutes.

The contacting may be conducted at 40 to 100° C., specifically 50 to 90° C., more specifically 60 to 80° C. to graft the polysaccharide to the water-dispersible, alkali-swellable crosslinked polyacrylate copolymer.

The emulsion comprising the water-dispersible, alkali-swellable crosslinked polyacrylate copolymer may be provided by contacting 20 to 75 weight percent of the α,β-ethylenically mono-unsaturated carboxylic acid monomer, 20 to 60 weight percent of the ethylenically unsaturated ester of (meth)acrylic acid, 0.01 to 1 weight percent of the crosslinking monomer comprising a polyunsaturated compound, a surfactant, the free-radical initiator, and water, each based on a total weight of the α,β-ethylenically mono-unsaturated carboxylic acid monomer, the ethylenically unsaturated ester of (meth)acrylic acid, and the crosslinking monomer; and polymerizing the α,β-ethylenically mono-unsaturated carboxylic acid monomer, the ethylenically unsaturated ester of (meth)acrylic acid, and the crosslinking monomer to form the emulsion comprising the water-dispersible, alkali-swellable crosslinked polyacrylate copolymer. The contacting may be conducted at 40 to 100° C., specifically 50 to 90° C., more specifically 60 to 80° C. to form the emulsion comprising the water-dispersible, alkali-swellable crosslinked polyacrylate copolymer. The α,β-ethylenically mono-unsaturated carboxylic acid monomer, the ethylenically unsaturated ester of (meth)acrylic acid, and the crosslinking monomer are further disclosed above.

In an embodiment wherein the polymerization is conducted in phases, in a second phase, e.g., a grafting phase, of the process, the presence of initiator in the second phase is optional. In an embodiment, the mole fraction of initiator may, for instance, be 0 to 30 wt %. In an embodiment, the mole fraction may be 0 to 28 wt %, alternatively 0 to 26 wt % of the total moles of initiator used in the entire polymerization and grafting process. An embodiment in which the initiator is omitted in the grafting phase is specifically mentioned.

The surfactant may comprise an anionic surfactant, a non-ionic surfactant, an amphoteric surfactant, a cationic surfactant, or a combination thereof. Use of an anionic surfactant and an amphoteric surfactant is specifically mentioned. The surfactant may be included in an amount of 0.1 wt % to 5 wt %, based on a total weight of the water-soluble, alkali-swellable crosslinked polyacrylate copolymer and the water dispersible polysaccharide. In another embodiment, the surfactant may be included in an amount of 0.1 wt % to 5 wt %, based on a total weight of the α,β-ethylenically mono-unsaturated carboxylic acid monomer, the ethylenically unsaturated ester of (meth)acrylic acid, and the crosslinking monomer.

Representative anionic surfactants for facilitating emulsion polymerization include, but are not limited to, sodium lauryl sulfate, ammonium lauryl sulfate, sodium lauryl ether sulfate, sodium myreth sulfate, sodium dodecyl benzene sulfonate, a sodium $C_6$ to $C_{15}$ alkyl phenoxy benzene sulfonate, a disodium $C_6$ to $C_{16}$ alkyl phenoxy benzene sulfonate, a disodium $C_6$ to $C_{16}$ di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, perfluorooctanesulfonate, perfluorobutanesulfonate, a phosphate ester of a branched alcohol ethoxylate, or a combination thereof.

Non-ionic surfactants suitable for facilitating emulsion polymerization include, but are not limited to, a linear or branched $C_8$ to $C_{30}$ fatty alcohol ethoxylate such as capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, behenyl alcohol ethoxylate, an alkylphenol alkoxylate such as octylphenol ethoxylate, a polyoxyethylene polyoxypropylene block copolymer, or a combination thereof. Representative fatty alcohol ethoxylates include a $C_8$ to $C_{22}$ fatty acid ester of polyoxyethylene glycol, an ethoxylated mono- and diglyceride, a sorbitan ester, an ethoxylated sorbitan ester, a $C_8$ to $C_{22}$ fatty acid glycol ester, a block copolymer of ethylene oxide and propylene oxide, or a combination thereof. The number of ethylene oxide units in each of the foregoing ethoxylates can range from 2 to about 150. Sodium lauryl sulfate, sodium laureth-3-sulfate, sodium dodecylbenzene sulfonate, and lauryl-ethoxylate-10, are specifically mentioned.

Representative amphoteric surfactants include amino acids, e.g., an N-alkyl amino acid or an N-acyl amino acid, a betaine such as cocamidopropyl betadine, a sultaine such as cocamidopropyl hydroxysultaine, an alkyl amphocarboxylate, lecithin, or a combination thereof.

The cationic surfactant can be, for example, an alkyl amine, alkyl imidazoline, ethoxylated amine, a quaternary ammonium compound, or a combination thereof. Examples of the alkylamine include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, amodimethicone, or a combination thereof. Examples of the alkyl imidazoline include an alkyl hydroxyethyl imidazoline such as stearyl hydroxyethyl imidazoline, coco hydroxyethyl imidazoline, ethyl hydroxymethyl oleyl oxazoline, or a combination thereof. Examples of the ethyloxylated amine include PEG-cocopolyamine, PEG-15 tallow amine, quaternium-52, or a combination thereof. Examples of the quarternary ammonium compound include cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(coconutalkyl)dimethyl ammonium chloride, ditallow dimethyl ammonium chloride, di(hydrogenated tallow) dimethyl ammonium chloride, di(hydrogenated tallow) dimethyl ammonium acetate, ditallow dimethyl ammonium methyl sulfate, ditallow dipropyl ammonium phosphate, ditallow dimethyl ammonium nitrate, or a combination thereof.

Also disclosed is a composition comprising the rheology modifier. The composition may be a pharmaceutical composition, cosmeceutical composition, or a cleaning composition. A cleaning composition, such as a laundry detergent, fabric softener, shampoo, or body wash, is specifically mentioned.

In addition to the rheology modifier, the composition may comprise an opacifier, a pearlescent additive, a pigment, an exfoliant, an anti-dandruff agent, a botanical agent, a preservative, a perfume, a propellant, a solvent, a diluent, an additional rheology modifier, or a combination thereof. The opacifier may be included to make the composition opaque. Examples include metal salts, such as aluminum or magnesium salts. Representative pearlescent additives include ethylene glycol monostearate, ethylene glycol distearate, $TiO_2$ coated mica, bismuth oxychloride, natural mother of pearl, or a combination thereof. The perfume may be encapsulated to provide an encapsulated additive. Representative pigments include titanium oxide, zinc oxide, aluminum oxide, iron oxide, manganese oxide, silicon oxide, silicates, cerium oxide, zirconium oxide, barium sulfate, or a combination thereof. Representative exfoliants include pumice, stone, zeolites, nut shells, nut meals, fruit pits, hulls, seeds and kernels, tea tree leaves, corn cob, fruit fibers, seaweed, loofah sponge, microcrystalline cellulose, bivalve shells, calcium carbonate, dicalcium pyrophosphate, chalk, silica, kaolin clay, silicic acid, aluminum oxide, stannic oxide, sea salt, talc, sugars, polyethylene, polystyrene, microcrystalline polyamides, microcrystalline polyesters, polycarbonates, stainless steel fibers, or a combination thereof. Representative anti-dandruff agents include sulfur, zinc pyrithione, zinc omadine, miconazole nitrate, selenium sulfide, piroctone olamine, N,N-bis(2-hydroxyethyl)undecenamide, cade oil, pine tar, Undecyleneth-6, or a combination thereof. Representative botanical agents include echinacea, yucca glauca, willow herb, basil leaves, Turkish oregano, carrot root, grapefruit, fennel seed, flax seed, rosemary, turmeric, thyme, blueberry, bell pepper, blackberry, spirulina, black currant fruit, tea leaves, such as for, example, Chinese tea, black tea, green tea, oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, witch hazel, or a combination thereof. Representative preservatives include polymethoxy bicyclic oxazolidine, methyl paraben, propyl paraben, ethyl paraben, butyl paraben, benzyltriazole, 1,3-dimethyl-5,5-dimethyl hydantoin, imidazolidinyl urea, phenoxyethanol, phenoxyethylparaben, methylisothiazolinone, methylchloroisothiazolinone, benzoisothiazolinone, triclosan, and suitable polyquarternium compounds disclosed above (e.g., Polyquaternium-1), or a combination thereof. Representative propellants include propane, butane, isobutene, ethers, dimethyl ether, halogenated hydrocarbons such as 1,1-difluoroethane, compressed gases such as air, carbon dioxide, or nitrogen, or a combination thereof. Representative solvents include water, an alcohol, a polyol, or a combination thereof. The solvent may be linear or branched, and examples include ethanol, propanol, isopropanol, hexanol, benzyl alcohol, cyclohexanol, a saturated $C_{12}$ to $C_{30}$ fatty alcohol such as lauryl alcohol, myristyl alcohol, cetyl alcohol, stearyl alcohol, or behenyl alcohol, glycerin, propylene glycol, butylene glycol, hexylene glycol, a $C_2$ to $C_4$ alkoxylated alcohol, a $C_2$ to $C_4$ alkoxylated polyol such as an ethoxylated, propoxylated, or butoxylated ethers of an alcohol, a polyol having 2 to about 30 carbon atoms and 1 to about 40 alkoxy units, polypropylene glycol, polybutylene glycol, or a combination thereof. Other examples of the solvent or diluent include a silicone such as cyclomethicone, a ketones such as acetone or methylethyl ketone, an oil such as a vegetable oil, plant oil, animal oil, essential oil, mineral oil, $C_7$ to $C_{40}$ isoparaffin, an alkyl carboxylic ester such as ethyl acetate, amyl acetate, ethyl lactate, jojoba oil, shark liver oil, or a combination thereof. The composition may comprise at least one of the foregoing.

Representative additional rheology modifiers include natural polymers, synthetic polymers, minerals, or salts. Examples of natural or modified natural polymers include a gum (e.g., xanthan gum), a cellulose, a modified cellulose, a starch, or a polysaccharide. Examples of synthetic polymers include a cross-linked polyacrylate, a hydrophobically modified alkali-soluble polymer, or a hydrophobically modified nonionic urethane polymer. Additionally, the adjustment of viscosity can be by admixture of a salt such as an alkali metal halide, or mineral such as a clay.

The opacifier, pearlescent additive, pigment, exfoliant, anti-dandruff agent, botanical agent, preservative, perfume, propellant, solvent, diluent, or additional rheology modifier can each independently be included in an amount of 0.01 to 99 wt %, specifically 0.1 to 95 wt %, more specifically 1 to 90 wt % of the composition, based on a total weight of the composition.

In an embodiment the composition is a body wash. In addition to the rheology modifier, the body wash may comprise water, the surfactant, a pH agent, the opacifier, the pearlescent additive, the pigment, the exfoliant, the anti-dandruff agent, the botanical agent, the preservative, the perfume, the propellant, the solvent, the diluent, or a combination thereof. In the body wash the rheology modifier may be included in an amount of 0.1 to 50 wt %, specifically 0.3 to 25 wt %, more specifically 0.6 to 12 wt %, or 0.9 to 6 wt %, or 1.2 to 3 wt %. The surfactant may be present in the body wash in an amount of 1 to 50 wt %, specifically 2 to 30 wt %, more specifically 4 to 25 wt %. The surfactant may comprise a cationic surfactant in an amount of 0.1 to 50 wt %, specifically 0.3 to 25 wt %, more specifically 0.6 to 20 wt %, or 0.9 to 15 wt %, or 1.2 to 10 wt %, and an amphoteric surfactant in an amount of 0.1 to 50 wt %, specifically 0.3 to 25 wt %, more specifically 0.6 to 12 wt %, or 0.9 to 6 wt %, or 1.2 to 3 wt %. Sodium laureth-3 suflate and cocamidopropyl betadine are specifically mentioned. The body wash may further comprise a solvent in an amount of 0.1 to 20 wt %, specifically 0.5 to 10 wt %, more specifically 1 to 5 wt %. Propylene glycol is specifically mentioned.

In an embodiment, a rheology modifier comprises a water-dispersible, alkali-swellable crosslinked polyacrylate copolymer comprising 0.02 to 5 weight percent of polysaccharide grafts, based on a total weight of the copolymer.

In another embodiment, a method of preparing a rheology modifier comprises: providing an emulsion comprising a water-dispersible, alkali-swellable crosslinked polyacrylate copolymer; and contacting the emulsion with an aqueous grafting solution comprising a water-soluble polysaccharide in the presence of a free-radical initiator to form an alkali-swellable crosslinked polysaccharide-grafted polyacrylate copolymer comprising 0.1 to 5 weight percent of polysaccharide grafts, based on a total weight of the copolymer, to form the rheology modifier.

In another embodiment, a composition comprises the rheology modifier.

In the various embodiments, (1) the rheology modifier comprises 20 to 75 weight percent of units derived from an α,β-ethylenically mono-unsaturated carboxylic acid monomer; 20 to 60 weight percent of units derived from an ethylenically unsaturated ester of (meth)acrylic acid; and 0.01 to 1 weight percent of crosslinks derived from a polyethylenically unsaturated crosslinker, each based on a total weight of the copolymer; and/or (2) the α,β-ethylenically mono-unsaturated carboxylic acid monomer is (meth)acrylic acid, maleic acid, itaconic acid, fumaric acid, crotonic acid, aconitic acid, or a combination thereof; and/or (3) the ethylenically unsaturated ester of (meth)acrylic acid is a C1 to C30 alkyl ester, a C1 to C30 arylalkyl ester, a C1 to C30 hydroxyalkyl ester, a C1 to C30 hydroxyarylalkyl ester, or a combination thereof; and/or (4) the ethylenically unsaturated ester of (meth)acrylic acid is methyl (meth)acrylate, ethyl acrylate, 2-ethylhexyl acrylate, butyl acrylate, benzyl acrylate, or a combination thereof; and/or (5) the crosslinker is trimethylolpropane diallyl ether, trimethylolpropane triallyl ether, diallyl phthalate, allyl methacrylate, or a combination thereof; and/or (6) the polysaccharide is a cellulose ether, a gum, a starch, or a combination thereof; and/or (7) the cellulose ether is hydroxyethyl cellulose, hydroxypropyl cellulose, hydroxyethyl methyl cellulose, hydroxypropyl methyl cellulose, hydroxypropylhydroxyethyl cellulose, carboxymethyl cellulose, carboxyethyl cellulose, or combination thereof; and/or (8) the cellulose ether is a hydroxyethyl cellulose having a viscosity of 1 to 5000 centipoise, when determined for a 2 weight percent aqueous solution comprising by Brookfield viscometry using a #1 spindle; and/or (9) the gum is guar gum, locust bean gum, xanthan gum, hydroxyethyl guar gum, methyl guar gum, ethyl guar gum, hydroxypropyl guar gum, hydroxyethylmethyl guar gum, hydroxypropylmethyl guar gum, or a combination thereof; and/or (10) the starch is methyl starch, ethyl starch, hydroxyethylmethyl starch, hydroxypropyl starch, hydroxypropylmethyl starch, or a combination thereof; and/or (11) the crosslinked polysaccharide-grafted polyacrylate copolymer further comprises 0.1 to 20 weight percent of units derived from a vinyl ester; and/or (12) the vinyl ester is vinyl acetate, vinyl neodecanoate, or a combination thereof; and/or (13) the alkali-swellable crosslinked polysaccharide-grafted polyacrylate copolymer comprises 20 to 75 weight percent of units derived from an α,β-ethylenically mono-unsaturated carboxylic acid monomer; and/or (14) the providing an emulsion comprising a water-dispersible, alkali-swellable crosslinked polyacrylate copolymer comprises: contacting 20 to 75 weight percent of an α,β-ethylenically mono-unsaturated carboxylic acid monomer, 20 to 60 weight percent of an ethylenically unsaturated ester of (meth)acrylic acid, 0.01 to 1 weight percent of a crosslinking monomer comprising a polyunsaturated compound, a surfactant, a free-radical initiator, and water, each based on a total weight of the α,β-ethylenically mono-unsaturated carboxylic acid monomer, the ethylenically unsaturated ester of (meth)acrylic acid, the crosslinking monomer; and polymerizing the α,β-ethylenically mono-unsaturated carboxylic acid monomer, the ethylenically unsaturated ester of (meth)acrylic acid, and the crosslinking monomer to form the emulsion comprising the water-dispersible, alkali-swellable crosslinked polyacrylate copolymer; and/or (15) the surfactant is present in an amount of 0.1 to 5 weight percent, based on a total weight of the α,β-ethylenically mono-unsaturated carboxylic acid monomer, the ethylenically unsaturated ester of (meth)acrylic acid, and the crosslinking monomer; and/or (16) the rheology modifier is in the form of an emulsion comprising the alkali-swellable crosslinked polysaccharide-grafted polyacrylate copolymer comprising 0.1 to 5 weight percent of polysaccharide grafts.

EXAMPLES

Rheological Analysis

Prior to rheological analysis the sample was centrifuged at 3,000 revolutions per minute (rpm) for 10 minutes (min). Dynamic oscillatory responses and flow rheology curves were collected using an AR-2000 rheometer (TA Instruments) using a 60 millimeter (mm) diameter stainless-steel cone with a 0.5° angle and a Peltier plate, run at 25° C.

Dynamic oscillatory rheology: Samples were conditioned by an initial shear of 5 per second ($s^{-1}$) for 5 minutes (min), followed by a 2 minute hold. Frequency was held constant at 1 Hertz (Hz), and the stress was incremented from 0.05 to 1000 Pascals (Pa), with 10 points per decade (logarithmically distributed). The point at which the elastic modulus equaled the storage modulus (G'=G") was calculated using the Rheology Advantage Data Analysis program (TA Instruments) and the crossover yield stress (YS, x-axis value) and G' value at crossover (y-axis value) were recorded.

Flow rheology: Samples were pre-stressed for 10 seconds (s) at 0.177 Pa and equilibrated for 2 min. Samples were subjected to increasing shear stress from 0.15 to 300 Pa, with 5 points per decade (logarithmically distributed), a tolerance of 3%, and a 3 min maximum point time. Values for viscosity at selected values of shear rate were interpolated from the datapoints using a $7^{th}$-order polynomial fit.

Particle Size Analysis

Particle sizes were measured on a Brookhaven Instrument Corporation 90PLUS Particle Size Analyzer, run in triplicate.

Polysaccharide Viscosity Analysis

The polysaccharides used in the examples were characterized by viscometry. They are all products of The Dow Chemical Company. Hydroxyethyl cellulose (HEC) was dispersed in deionized water at 2 wt % and dosed with a few drops of 10% NaOH solution to form a clear solution. Measurements of viscosity were done on a Brookfield DV-II+ Viscometer utilizing spindle #1. Table 1 shows the Brookfield viscosities for HEC polymers at three different spindle speeds.

TABLE 1

|  | Spindle Speed | | |
|---|---|---|---|
| Hydroxyethyl cellulose | 60 RPM | 30 RPM | 12 RPM |
| CELLOSIZE ® QP 3L | 11.2 | 23.4 | 28.5 |
| CELLOSIZE ® QP 9L | 11.2 | 18.4 | 20 |
| CELLOSIZE ® QP 40 | 78.8 | 47.2 | 91 |

Example 1

To a three liter round bottom flask equipped with a mechanical stirrer, a heating mantle, a thermocouple, a condenser and inlets for the addition of monomer, initiator, and nitrogen was charged 489 grams (g) of deionized water. The water was stirred with a nitrogen flow and heated to 92-94° C. To a plastic lined vessel, 32.13 g of 28% sodium lauryl sulfate (SLS) and 721 g deionized water were added and mixed by overhead stirring. Ethyl acrylate (EA, 302.35 g) was charged to the vessel followed by 27 g ethylhexyl acrylate (EHA), 16.19 g vinyl neodecanoate (VEOVA), 0.77 g trimethylolpropane diallyl ether (90% active, TMPDE-90) and 194.36 g methacrylic acid (MAA) to form a smooth, stable monomer emulsion. An initiator charge was prepared by dissolving 0.197 g of ammonium persulfate (APS) in 12 g deionized water and set aside. An initiator solution of 0.9 g APS dissolved in 63.8 g deionized water was added to a syringe.

When the flask contents reached the target temperature of 91-94° C., a portion of the monomer emulsion (129.4 g) was added to the flask via a pump, followed by the initiator charge. After 1 min, the temperature in the flask began to rise. After a peak exotherm, the monomer emulsion was added over 90 min at the following rates: 7.76 g/min for 15 min, then 13.97 g/min for 75 min, and at the same time the initiator solution was added at the following rates: 0.42 g/min for 15 min, then 0.93 g/min for 75 min. The reaction mixture was then held for 15 min at 90-92° C.

Separately the polysaccharide grafting solution was prepared. To a plastic lined vessel, 160 g of deionized water and 3 g 28% SLS were added and stirred by overhead mixing. Hydroxyethyl cellulose (HEC, CELLOSIZE® QP-3L, 3.0 g) and 33.6 g EA were added to the vessel followed by 3 g EHA, 1.8 g VEOVA and 21.6 g MAA to form a smooth, stable monomer emulsion. A grafting initiator solution was prepared from 0.09 g ammonium persulfate and 15 g deionized water and added to a syringe for addition to the flask.

After completion of the 15 min hold, the polysaccharide grafting and grafting initiator solutions were added over 30 min at 90° C. A rinse of 10 g deionized water was added and the reaction was then held for 30 min.

First chase activator and first chase catalyst solutions were prepared by dissolving 0.92 g of 70% t-butyl hydroperoxide (tBHP) in 15 g deionized water and 0.59 g isoascorbic acid (IAA) in 15 g deionized water. When the grafting hold was completed, the first chase solutions were added over 15 min at 90° C. and the mixture held for 15 min after completion of the addition. Separately, second chase activator and second chase catalyst solutions were prepared by dissolving 0.68 g of 70% tBHP in 10 g deionized water and 0.42 IAA in 10 g deionized water. At the completion of the addition of the first chase solutions, 100 g deionized water was added to the flask and the reaction was allowed to cool. The second chase solutions were added over 15 min. After a 15 min hold, the reaction was cooled to room temperature and the contents were then filtered through a 100 mesh bag.

The solids content of the sample was 27.30 wt %. The coagulate level was 125 ppm. Average particle size was 131 nm. The content of residual EA was below detection limit and the content of EHA was 7 ppm.

Comparative Example C1

Example 1 was repeated except that HEC was excluded from the polysaccharide grafting solution. The solids content of the sample was 28.02 wt %. The coagulate level was 350 ppm. Average particle size was 113 nm. The content of residual EA was 0.2 ppm and the content of EHA was 7 ppm.

Example 2

Example 1 was repeated with the exception of the monomer emulsion and HEC grafting solution. To a plastic lined vessel, 32.13 g of 28% SLS and 721 g deionized water was added and mixed by overhead stiffing. 77.14 g of a surfactant monomer mixture containing methacrylate ester of a 20-ethoxylate of cetyl-stearyl alcohol (70 wt %), MAA (20 wt %), and 10 wt % deionized water, hereinafter "MA-20", and 248.4 g EA were charged to the vessel, followed by slow addition of 27 g EHA, 16.19 g VEOVA, 0.69 g TMPDE-90, and 179.08 g of MAA to form a smooth, stable monomer emulsion.

The polysaccharide grafting solution was prepared by adding 3 g HEC QP-3L to 160 g deionized water, followed by 3 g 28% sodium lauryl sulfate and stirring by overhead mixing. MA-20 (8.57 g), EA (27.6 g) were charged to the vessel followed by 3 g EHA, 1.8 g VEOVA, 19.88 g MAA and 0.062 g TMPDE-90 to form a smooth, stable monomer emulsion. The solids content of the sample was 26.30 wt %. The coagulate level was 1750 ppm. Average particle size was 172 nm. The content of residual EA was 2 ppm and the content of EHA was 3 ppm.

Comparative Example C2

Example 2 was repeated except that HEC was excluded from the polysaccharide grafting solution. The solids content of the sample was 27.16 wt %. The coagulate level was 1700 ppm. Average particle size was 128 nm. The content of residual EA was below the detection limit and the content of EHA was 0.9 ppm.

Example 3

Example 1 was repeated except that the SLS in the monomer emulsion was replaced by 51 g sodium dodecylbenzenesulfonate (SDBS, 22%) and the SLS in the polysaccharide graft solution was replaced by 3 g SDBS (22%). The solids content of the sample was 26.80 wt %. The coagulate content was 204 ppm. Average particle size was 136 nm. The content of residual EA was below detection limit and that of EHA was 1.0 ppm.

Comparative Example C3

Example 3 was repeated except that HEC was excluded from the polysaccharide grafting solution. The solids content of the sample was 27.30 wt %. The coagulate content was 360 ppm. Average particle size was 106 nm. The content of residual EA was below detection limit and the content of EHA was 5 ppm.

Example 4

To a three liter round bottom flask equipped with a mechanical stirrer, heating mantle, thermocouple, condenser and inlets for the addition of monomer, initiator and nitrogen were charged 489 g deionized water. The water was stirred with a nitrogen flow and heated to 92-94° C. To a plastic lined vessel, 32.13 g of SLS (28%) and 721 g deionized water were added and mixed by overhead stirring. EA (302.35 g) was charged to the vessel followed by 27 g EHA, 16.19 g VEOVA, 0.77 g TMPDE-90 and 194.36 g MAA to form a smooth, stable monomer emulsion. An initiator charge was prepared from 0.197 g APS and 12 g deionized water and set aside. An initiator solution of 0.9 g APS dissolved in 63.8 g deionized water was added to a syringe.

When the flask contents reached the target temperature of 91-94° C., a portion of the monomer emulsion (129.4 g) was added to the flask via a pump, followed by the initiator. After 1 min, the temperature in the flask began to rise. After a peak exotherm, the monomer emulsion was added over 90 min at the following rates: 7.5 g/min for 15 min, then 16.6 g/min for 75 min, and at the same time the initiator was added at the following rates: 0.41 g/min for 15 min, then 0.92 g/mins for 75 min. At the completion of the rinses, the reaction was then held for 15 min at 90-92° C.

Separately, the polysaccharide grafting solution was prepared. To a plastic lined vessel, 160 g of deionized water and 9 g 28% SLS were added and stirred by overhead mixing. HEC QP-3L (3.0 g) and 33.6 g EA were charged to the vessel followed by 3 g EHA, 1.8 g VEOVA and 21.6 g MAA to form a smooth, stable monomer emulsion. A grafting initiator solution was prepared from 0.09 g APS and 15 g deionized water and added to a syringe for addition to the flask.

At the completion of the 15 min hold, the grafting and grafting initiator solutions were added over 30 min at while the temperature was allowed to fall from 90 to 78° C. A rinse of 10 g deionized water was added and the reaction was then held for 15 min.

First chase activator and first chase catalyst solutions were prepared by dissolving 0.92 g of 70% tBHP in 15 g deionized water and 0.59 g IAA in 15 g deionized water. When the 15 min grafting hold was completed, the first chase solutions were added over 30 min while the temperature was allowed to fall from 78 to 65° C. Separately, second chase activator and second catalyst solutions were prepared by dissolving 0.68 g of 70% tBHP in 10 g deionized water and 0.42 IAA in 10 g deionized water. At the completion of addition of the first chase solutions, 100 g of deionized water was added to the flask and the reaction was allowed to cool. The second chase solutions were added over 30 min while the temperature was allowed to fall from 65 to 50° C. After the reactor contents had cooled to room temperature they were filtered through a 100 mesh bag.

The solids content of the sample was 27.0 wt %. The coagulate content was approximately 300 ppm. Average particle size was 195 nm. The content of residual EA was below detection limit and the content of EHA was 5 ppm.

Comparative Example C4

Example 4 was repeated except that HEC was excluded from the polysaccharide grafting solution. The solids content of the sample was 27.30 wt %. The coagulate content was less than 300 ppm. Average particle size was 111 nm. The content of residual EA was 373 ppm and the content of EHA was 70 ppm.

Aqueous Solutions of Rheology Modifiers

Solutions of polymers (0.75 wt %) made in Example 4 and Comparative Example C4 were prepared as follows:

Example 5

To 160.00 g deionized water was added 5.5572 g of the emulsion from Ex. 4, 5.0309 g NaOH (4.8 wt %), and 29.34 g additional water was added with overhead stirring at 450 RPM at room temperature, with the final mixture stirred for 25 min. The pH of the solution was 8.45 and the turbidity was 49 NTU.

Comparative Example 5

To 159.99 g deionized water was added 5.2850 g of the emulsion from Comparative Example C4, 23.2 mg HEC QP-3L, 4.9532 g NaOH (4.8%), and 29.62 g additional water with overhead stiffing at 450 RPM at room temperature, with the final mixture stirred for 25 min. The pH of the solution was 8.31 and the turbidity was 91 NTU.

The aqueous solutions of Example 5 and Comparative Example 5 were left to stand in a covered glass jar for 4 days. After 4 days, the aqueous solution of Example 5, containing the grafted polysaccharide, retained bubbles that appeared during preparation, whereas the aqueous solution of Comparative Example 5, containing ungrafted polysaccharide at the same weight content as in Example 5, did not retain any bubbles.

Example 6

Example 1 was repeated with the following modifications: 9 g of HEC QP-3L was used instead of 3 g; allyl methacrylate (ALMA) was used instead of TMPDE (0.693 g in the monomer emulsion and 0.077 g in the grafting solution). The solids content of the sample was 26.36 wt %. The coagulate content was 210 ppm. Average particle size was 312 nm. The content of residual EA was below detection limit and the content of EHA was 5 ppm.

Comparative Example C6

Example 6 was repeated except that HEC was excluded from the polysaccharide grafting solution. The solids content of the sample was 26.14 wt %. The coagulate content was 300 ppm. Average particle size was 113 nm. The content of residual EA was below detection limit and the content of EHA was 5 ppm.

Aqueous Solutions of Rheology Modifiers

Solutions of polymers (0.75 wt %) made in Example 6 and Comparative Example C6 were prepared as follows:

Example 7

To 159.98 g deionized water was added 5.66 g of the emulsion from Ex. 6, 4.886 g NaOH (4.8%), and 29.46 g additional water with overhead stirring at 300 RPM at room temperature, with the final mixture stirred for 25 min. The pH of the solution was 8.58 and the turbidity was 182 NTU.

Comparative Example 7

To 160.04 g deionized water was added 5.746 g of the emulsion from Comparative Example C6, 4.9532 g NaOH (4.8%), and 29.28 g additional water with overhead stirring at 300 RPM at room temperature, with the final mixture stirred for 25 min. The pH of the solution was 8.53 and the turbidity was 184 NTU.

Example 7 and Comparative Example 7 were left to stand in a covered glass jar for 6 days. After 6 days, Example 7, containing the grafted polysaccharide, retained bubbles that appeared during preparation, whereas Comparative Example 7, which did not include the polysaccharide, did not retain any bubbles.

Example 8

Example 2 was repeated except the 32.13 g SLS was used instead of the 51.9 g SDBS in the monomer emulsion, and the 3 g of SLS in the grafting solution was used instead of the 3 g SDBS. A polysaccharide solution HEC QP-3L was used instead of the 3 g HEC QP 09L. The coagulate content was 200 ppm. Average particle size was 131 nm. The content of residual EA was 7 ppm and the content of EHA was 6 ppm.

Example 9

Example 1 was repeated except the 32.13 g SLS was used instead of the 51.9 g SDBS in the monomer emulsion and the 3 g of SLS in the grafting solution was used instead of the 3 g SDBS. A polysaccharide solution of HEC QP-3L was used instead of the 3 g HEC QP 40. The coagulate level was 200 ppm. Average particle size was 138 nm. The content of EA was below the detection limit and that of the EHA was 6 ppm.

Preparation of Body-Wash Formulations

The polymers of Examples 1-4, 6, and 8-9 and Comparative Examples C1 to C4 and C6 were used to prepare body wash cleansing formulations as follows. To a glass jar were first added deionized water and then an amount of polymer emulsion to provide 2 wt % of the polymer. In the body-wash formulations including C3 and C4, polysaccharide was also introduced as a dry powder. Next, sodium laureth-3 sulfate (SLES, STEOL® CS-370 E, 70.4%, Stepan Co.) was added to each with overhead stiffing at 300 RPM and stirred for at least 20 min and until a solution was formed. Next, 0.55 g of sodium hydroxide (11.50 g of a 4.8 wt % solution or 9.84 g of a 5.61 wt % solution) was added to neutralize the polymer to a target extent. Stirring was continued at 300 RPM for another 10 min. Next, cocamidopropyl betaine (CAPB, Amphosol® CA, 30%, Stepan Co.) was added and stirred for 5 min, followed by the addition of propylene glycol (PG), with stiffing for an additional 3 min. Deionized water was added next to bring the total weight to a target of 150 g. The ingredients were chosen to give a final composition as represented in Table 2.

TABLE 2

Composition of body-wash formulations.

| Ingredient | Weight Percent |
|---|---|
| Polymer | 2.0 |
| SLES | 10.0 |
| CAPB | 3.0 |
| PG | 2.0 |
| water | 83.0 |

Rheological Analysis

Figure 3:
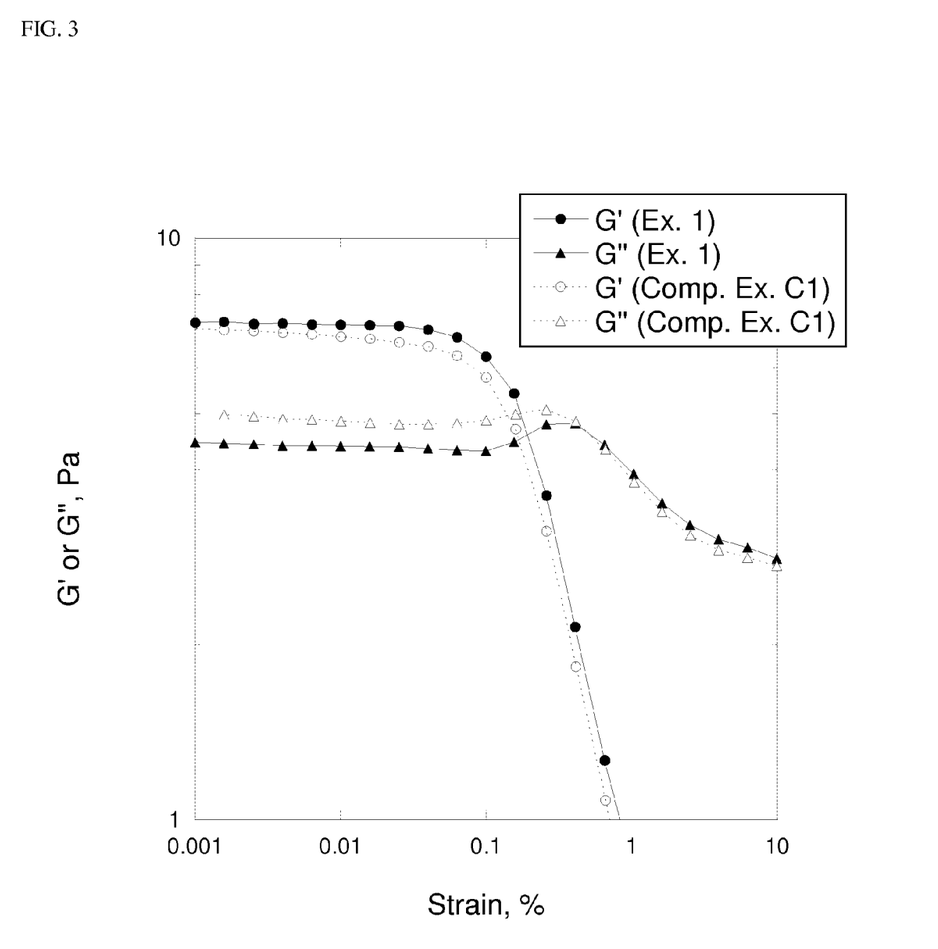
FIG. 3 is a graph of elastic modulus (G', circles, Pascals, Pa) and storage modulus (G", triangles, Pascals, Pa) versus strain (percent, %) of body wash formulations of the polymers of Example 1 (shaded symbols) and Comparative Example 1 (open symbols)

Table 3 provides the results of rheological analysis of the polymer solutions in water and in body-wash formulations. In Table 3, Polym. (wt %) is the content of polymer in the formulation in weight percent, Type indicates if the formulation is in water or a body wash (b/w) formulation, η is viscosity, G' is elastic modulus, and G" is storage modulus. In the comparative examples, Cellosize HEC QP-3L, was added separately to the formulation directly after addition of the polyacrylate copolymer emulsion and not grafted. In the body wash of Comparative Example C3, the HEC was added in the form of a 5 wt % in water. In the body wash of Comparative Example C4, the HEC was added in the form of a dry powder. In Table 3, "HEC added post-polymerization (ppm)" is based on dry HEC weight.

the polymer of Example 1 (open symbols) and Comparative Example 1 (shaded symbols), as determined by oscillatory rheologic analysis. The elastic modulus (G') of the formulation including the polymer of Example 1 (shaded circles) was similar at low strain and greater at higher strain when compared to the formulation including the polymer of Comparative Example 1 (open circles). The storage modulus (G") of the formulation including the polymer of Example 1 (shaded triangles) was less at low strain, similar at intermediate strain, and greater at higher strain, when compared to the formulation including the polymer of Comparative Example 1 (open triangles).

Figure 4:
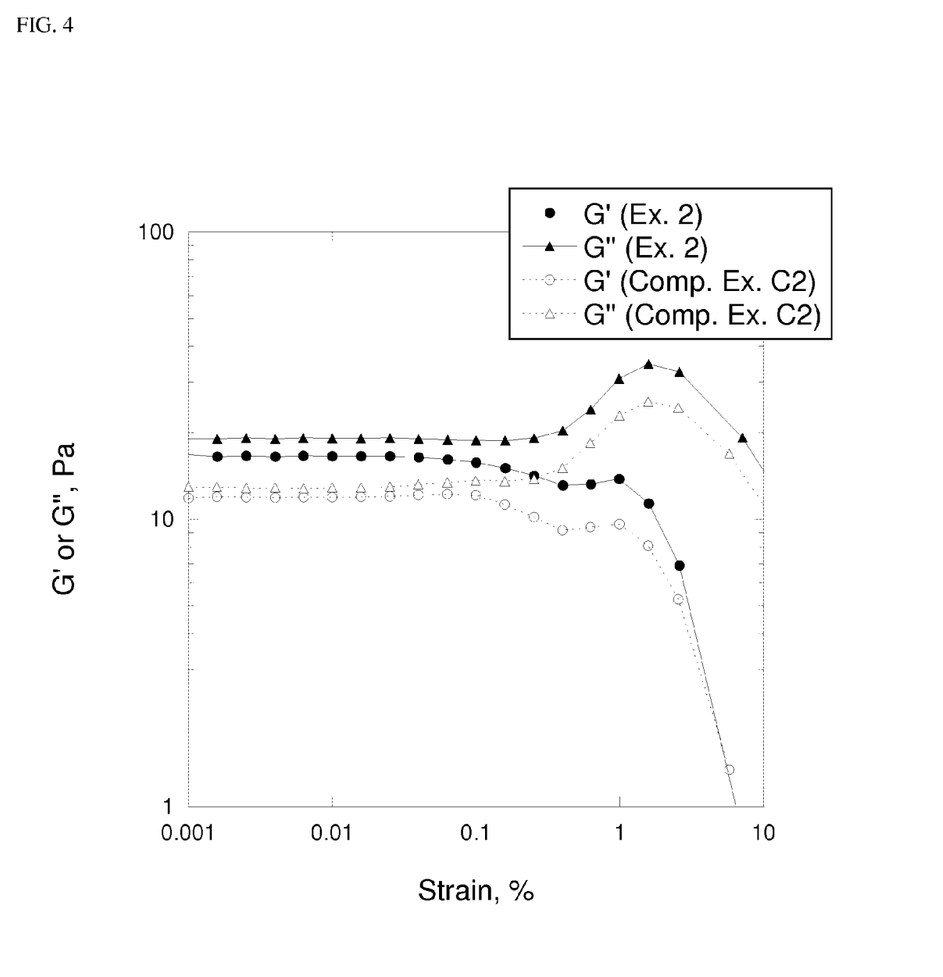
FIG. 4 is a graph of elastic modulus (G', circles, Pascals, Pa) and storage modulus (G", triangles, Pascals, Pa) versus strain (percent, %) of body wash formulations of the polymers of Example 2 (shaded symbols) and Comparative Example 2 (open symbols).

FIG. 4 shows the elastic moduli (circles) and storage moduli (triangles) of the body wash formulations containing the polymer of Example 2 (open symbols) and Comparative Example 2 (shaded symbols), as determined by oscillatory rheologic analysis. The elastic modulus (G') of the formulation including the polymer of Example 2 (shaded circles) was greater at low strain and similar at higher strain when compared to the formulation including the polymer of Comparative Example 1 (open circles). The storage modulus (G") of the formulation including the polymer of Example 2 (shaded triangles) was greater than the formulation including the polymer of Comparative Example 1 (open triangles), and the difference in the storage moduli was greatest at low strain.

"Alkyl" as used herein means a straight or branched chain saturated aliphatic hydrocarbon having the specified number

TABLE 3

| Polymer | Polym. (%) | Form. Type | Add'l HEC (ppm) | pH | Turbidity (NTU) | η (Pa·s) @ 0.01 s$^{-1}$ | η (Pa·s) @ 1 s$^{-1}$ | η (Pa·s) @ 20 s$^{-1}$ | η (Pa·s) @ 200 s$^{-1}$ | G' (Pa) @ 1% strain | G" (Pa) @ 1% strain | G' @ crossover | strain (%) at crossover |
|---|---|---|---|---|---|---|---|---|---|---|---|---|---|
| 1 | 0.75 | water | 0 | 8.33 | 66 | — | — | — | — | 27.80 | 5.69 | 7.27 | 21.46 |
| C1 | 0.75 | water | 0 | 8.51 | — | — | — | — | — | 18.93 | 4.11 | 5.41 | 23.58 |
| 1 | 2 | b/w | 0 | 7.42 | 7.7 | 23.9 | 1.85 | 0.84 | 0.44 | 6.97 | 4.39 | 4.59 | 19.23 |
| C1 | 2 | b/w | 0 | 7.25 | 9 | 19.06 | 1.74 | 0.78 | 0.43 | 6.65 | 4.84 | 4.95 | 14.18 |
| 2 | 2 | b/w | 0 | 7.37 | 8.3 | 51.65 | 13.65 | 5.74 | 0.91 | 16.49 | 19.16 | n/a | n/a |
| C2 | 2 | b/w | 0 | 7.4 | 14.3 | 36.13 | 8.53 | 4.48 | 0.69 | 11.91 | 12.86 | n/a | n/a |
| 3 | 2 | b/w | 0 | 7.47 | 8.5 | 41.43 | 2.58 | 1.03 | 0.49 | 11.43 | 6.73 | 6.74 | 20.06 |
| C3 | 2 | b/w | 114 | 7.5 | 5.4 | 33.37 | 2.26 | 0.85 | 0.45 | 10.18 | 6.05 | 6.81 | 17.35 |
| 4 | 0.75 | water | 0 | 8.45 | 49 | — | — | — | — | 28.92 | 4.70 | 7.38 | 23.54 |
| C4 | 0.75 | water | 116 | 8.31 | 91 | — | — | — | — | 26.49 | 5.06 | 6.66 | 22.58 |
| 4 | 2 | b/w | 0 | 7.96 | — | — | — | — | — | 8.49 | 5.44 | 5.87 | 17.42 |
| C4 | 2 | b/w | 300 | 7.85 | — | — | — | — | — | 8.78 | 5.92 | 6.04 | 18.82 |
| 6 | 0.75 | water | 0 | 8.58 | 182 | — | — | — | — | 8.36 | 2.23 | 3.02 | 18.82 |
| C6 | 0.75 | water | 0 | 8.53 | 184 | — | — | — | — | 5.87 | 2.00 | 2.65 | 18.86 |
| 6 | 2 | b/w | 0 | 7.42 | 14.7 | — | — | — | — | 1.15 | 1.89 | n/a | n/a |
| C6 | 2 | b/w | 0 | 7.23 | 18 | — | — | — | — | 0.59 | 1.63 | n/a | n/a |
| 8 | 2 | b/w | 0 | 7.32 | 7.4 | 41.09 | 2.54 | 1.03 | 0.50 | 10.78 | 6.35 | 6.94 | 19.06 |
| 9 | 2 | b/w | 0 | 7.25 | 9.1 | 44.87 | 2.88 | 1.16 | 0.54 | 10.99 | 6.72 | 7.56 | 19.40 |

Figure 1:
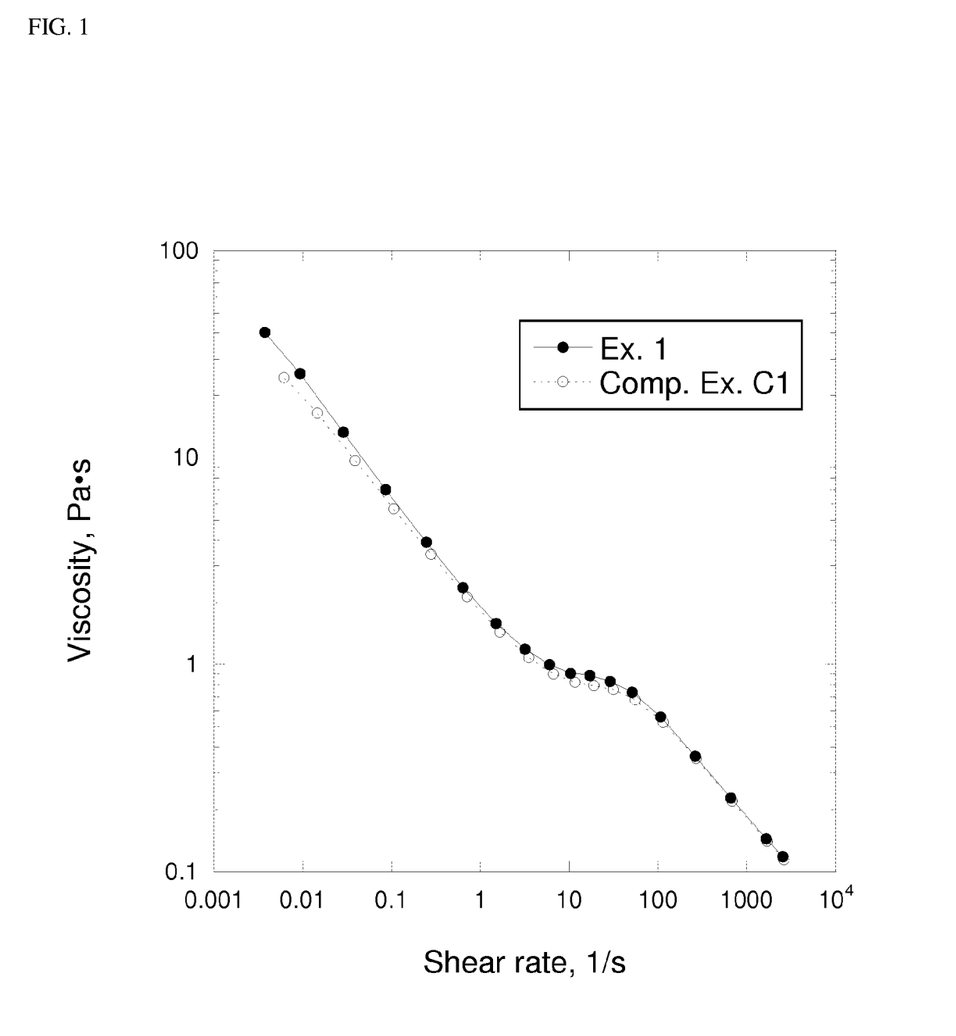
FIG. 1 is a graph of viscosity (Pascal-seconds, Pa·s) versus shear rate (per second, 1/s) of body wash formulations of the polymers of Example 1 (shaded circles) and Comparative Example 1 (open circles)

FIG. 1 shows the results of rheologic analysis of the body wash formulations containing the polymers of Example 1 (shaded circles) and Comparative Example C1 (open circles). At low shear rates, e.g., 0.01 s$^{-1}$, the formulation with the polymer of Example 1 had significantly increased viscosity, whereas at a high shear rate, e.g., 1000 s$^{-1}$, the formulations provided similar viscosity.

Figure 2:
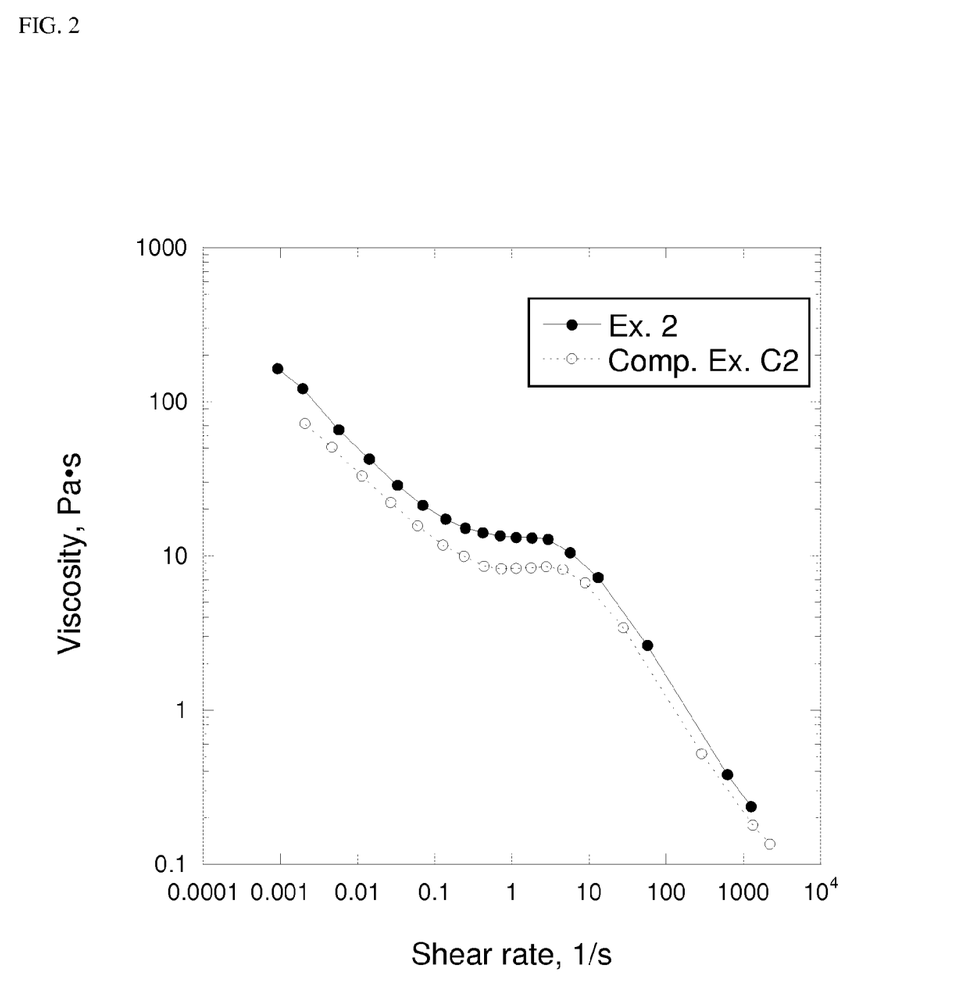
FIG. 2 is a graph of viscosity (Pascal-seconds, Pa·s) versus shear rate (per second, 1/s) of body wash formulations of the polymers of Example 2 (shaded circles) and Comparative Example 2 (open circles)

FIG. 2 shows the results of rheologic analysis of the body wash formulations containing the polymers of Example 2 (shaded circles) and Comparative Example C2 (open circles). At low shear rates, e.g., 0.01 s$^{-1}$, the formulation with the polymer of Example 2 had significantly increased viscosity, whereas at a high shear rate, e.g., 1000 s$^{-1}$, the formulations provided similar viscosity.

FIG. 3 shows the elastic moduli (circles) and storage moduli (triangles) of the body wash formulations containing of carbon atoms, specifically 1 to 12 carbon atoms, more specifically 1 to 6 carbon atoms.

"Aryl" as used herein means a cyclic moiety in which all ring members are carbon and at least one ring is aromatic, the moiety having the specified number of carbon atoms, specifically 6 to 24 carbon atoms, more specifically 6 to 12 carbon atoms. More than one ring may be present, and any additional rings may be independently aromatic, saturated or partially unsaturated, and may be fused, pendant, spirocyclic or a combination thereof.

"Arylalkyl" as used herein means an aryl group covalently linked to an alkyl group that is linked to a compound (e.g., a benzyl is a C7 arylalkyl group).

"Alkylene" as used herein means a straight, branched or cyclic divalent aliphatic hydrocarbon group, and may have from 1 to about 18 carbon atoms, more specifically 2 to about 12 carbons. Exemplary alkylene groups include methylene (—CH$_2$—), ethylene (—CH$_2$CH$_2$—), propylene (—(CH$_2$)$_3$—), or cyclohexylene (—C$_6$H$_{10}$—).

"(Meth)acrylic" is inclusive of acrylic and methacrylic, and "(meth)acrylate is inclusive of acrylate and methacrylate.

The invention claimed is:

1. A rheology modifier comprising:
a water-dispersible, alkali-swellable crosslinked polyacrylate copolymer comprising 0.02 to 5 weight percent of polysaccharide grafts, based on a total weight of the copolymer.

2. The rheology modifier of claim 1, comprising:
20 to 75 weight percent of units derived from an α,β-ethylenically mono-unsaturated carboxylic acid monomer;
20 to 60 weight percent of units derived from an ethylenically unsaturated ester of (meth)acrylic acid; and
0.01 to 1 weight percent of crosslinks derived from a polyethylenically unsaturated crosslinker,
each based on a total weight of the copolymer.

3. The rheology modifier of claim 2, wherein the α,β-ethylenically mono-unsaturated carboxylic acid monomer is (meth)acrylic acid, maleic acid, itaconic acid, fumaric acid, crotonic acid, aconitic acid, or a combination thereof.

4. The rheology modifier of claim 2, wherein the ethylenically unsaturated ester of (meth)acrylic acid is a C1 to C30 alkyl ester, a C1 to C30 arylalkyl ester, a C1 to C30 hydroxyalkyl ester, a C1 to C30.

5. The rheology modifier of claim 3, wherein the ethylenically unsaturated ester of (meth)acrylic acid is methyl (meth)acrylate, ethyl acrylate, 2-ethylhexyl acrylate, butyl acrylate, benzyl acrylate, or a combination thereof.

6. The rheology modifier of claim 2, wherein the crosslinker is trimethylolpropane diallyl ether, trimethylolpropane triallyl ether, diallyl phthalate, allyl methacrylate, or a combination thereof.

7. The rheology modifier of claim 1, wherein the polysaccharide is a cellulose ether, a gum, a starch, or a combination thereof.

8. The rheology modifier of claim 7, wherein the cellulose ether is hydroxyethyl cellulose, hydroxypropyl cellulose, hydroxyethyl methyl cellulose, hydroxypropyl methyl cellulose, hydroxypropylhydroxyethyl cellulose, carboxymethyl cellulose, carboxyethyl cellulose, or combination thereof.

9. The rheology modifier of claim 8, wherein the cellulose ether is a hydroxyethyl cellulose having a viscosity of 1 to 5000 centipoise, when determined for a 2 weight percent aqueous solution comprising by Brookfield viscometry using a #1 spindle.

10. The rheology modifier of claim 7, wherein the gum is guar gum, locust bean gum, xanthan gum, hydroxyethyl guar gum, methyl guar gum, ethyl guar gum, hydroxypropyl guar gum, hydroxyethylmethyl guar gum, hydroxypropylmethyl guar gum, or a combination thereof.

11. The rheology modifier of claim 7, wherein the starch is methyl starch, ethyl starch, hydroxyethylmethyl starch, hydroxypropyl starch, hydroxypropylmethyl starch, or a combination thereof.

12. The rheology modifier of claim 1, wherein the crosslinked polysaccharide-grafted polyacrylate copolymer further comprises 0.1 to 20 weight percent of units derived from a vinyl ester.

13. The rheology modifier of claim 12, wherein the vinyl ester is vinyl acetate, vinyl neodecanoate, or a combination thereof.

14. A method of preparing a rheology modifier, the method comprising:
providing an emulsion comprising a water-dispersible, alkali-swellable crosslinked polyacrylate copolymer; and
contacting the emulsion with an aqueous grafting solution comprising a water-dispersible polysaccharide in the presence of a free-radical initiator to form an alkali-swellable crosslinked polysaccharide-grafted polyacrylate copolymer comprising 0.1 to 5 weight percent of polysaccharide grafts, based on a total weight of the copolymer, to form the rheology modifier.

15. The method of claim 14, wherein the alkali-swellable crosslinked polysaccharide-grafted polyacrylate copolymer comprises 20 to 75 weight percent of units derived from an α,β-ethylenically mono-unsaturated carboxylic acid monomer.

16. The method of claim 14, wherein the providing an emulsion comprising a water-dispersible, alkali-swellable crosslinked polyacrylate copolymer comprises:
contacting
20 to 75 weight percent of an α,β-ethylenically mono-unsaturated carboxylic acid monomer,
20 to 60 weight percent of an ethylenically unsaturated ester of (meth)acrylic acid,
0.01 to 1 weight percent of a crosslinking monomer comprising a polyunsaturated compound,
a surfactant, a free-radical initiator, and water, each based on a total weight of the α,β-ethylenically mono-unsaturated carboxylic acid monomer, the ethylenically unsaturated ester of (meth)acrylic acid, the crosslinking monomer; and
polymerizing the α,β-ethylenically mono-unsaturated carboxylic acid monomer, the ethylenically unsaturated ester of (meth)acrylic acid, and the crosslinking monomer to form the emulsion comprising the water-dispersible, alkali-swellable crosslinked polyacrylate copolymer.

17. The method of claim 16, wherein the surfactant is present in an amount of 0.1 to 5 weight percent, based on a total weight of the α,β-ethylenically mono-unsaturated carboxylic acid monomer, the ethylenically unsaturated ester of (meth)acrylic acid, and the crosslinking monomer.

18. The method of claim 14, wherein the rheology modifier is in the form of an emulsion comprising the alkali-swellable crosslinked polysaccharide-grafted polyacrylate copolymer comprising 0.1 to 5 weight percent of polysaccharide grafts.

19. A composition comprising the rheology modifier of claim 1.

* * * * *